United States Patent [19]

Martin

[11] Patent Number: 5,201,708
[45] Date of Patent: Apr. 13, 1993

[54] SELF-LOCKING SAFETY SYRINGE
[75] Inventor: Robin Martin, McAllen, Tex.
[73] Assignee: Timothy A. Kershenstine, Metairie, La.
[21] Appl. No.: 829,708
[22] Filed: Feb. 3, 1992
[51] Int. Cl.⁵ .............................................. A61M 5/00
[52] U.S. Cl. ..................................... 604/110; 604/198
[58] Field of Search ............... 604/198, 263, 187, 192, 604/110

[56] References Cited
U.S. PATENT DOCUMENTS

| | | | |
|---|---|---|---|
| 4,894,055 | 1/1990 | Sudnak | 604/198 |
| 4,923,447 | 5/1990 | Morgan | 604/198 |
| 4,927,416 | 5/1990 | Tomkiel | 604/198 |

Primary Examiner—John D. Yasko
Attorney, Agent, or Firm—Keaty & Keaty

[57] ABSTRACT

The invention relates to a safety syringe to prevent accidental puncturing of attending medical personnel by an infected syringe needle. The safety syringe has an elongated tubular casing, which houses an elongated needle guard, which is telescopically connected to the casing and is mounted in co-axial alignment with the casing. A syringe barrel is co-axially mounted within the needle guard, the syringe barrel carrying a needle assembly on one of its ends, and an end plate on its opposite end. The end plate "snaps" into a groove formed in a transverse flange of the casing, fixedly attaching the syringe barrel to the casing. A sealing plate covers the locked end plate by engaging within another groove formed in the flange. One or more resileint depressible locking tabe are carried by the needle guard and extend through corresponding aligned openings formed in the casing to lock the needle guard in an extended position covering the needle. When the locking tabs are depressed, and an inward pressure is exerted on the forward end of the needle guard, the needle guard can be moved against the tension of a coil spring inside the casing and uncover the syringe needle to allow withdrawing of medication from the medicine bottle, or performing of an injection.

20 Claims, 4 Drawing Sheets

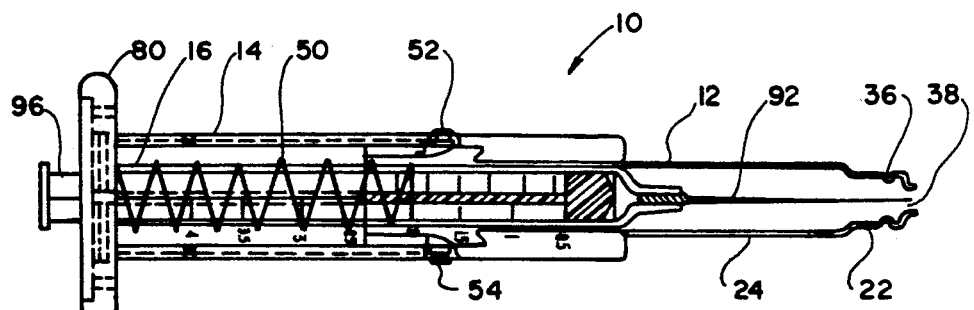
F I G . 1
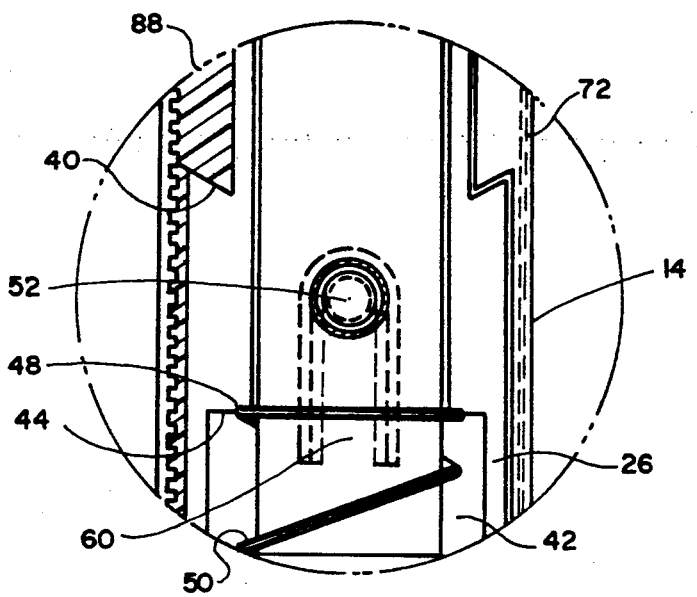
F I G . 2
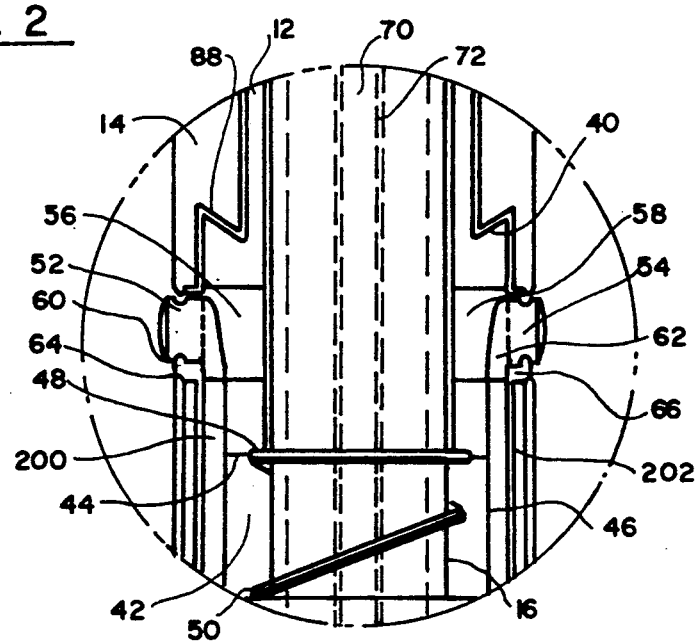
F I G . 3

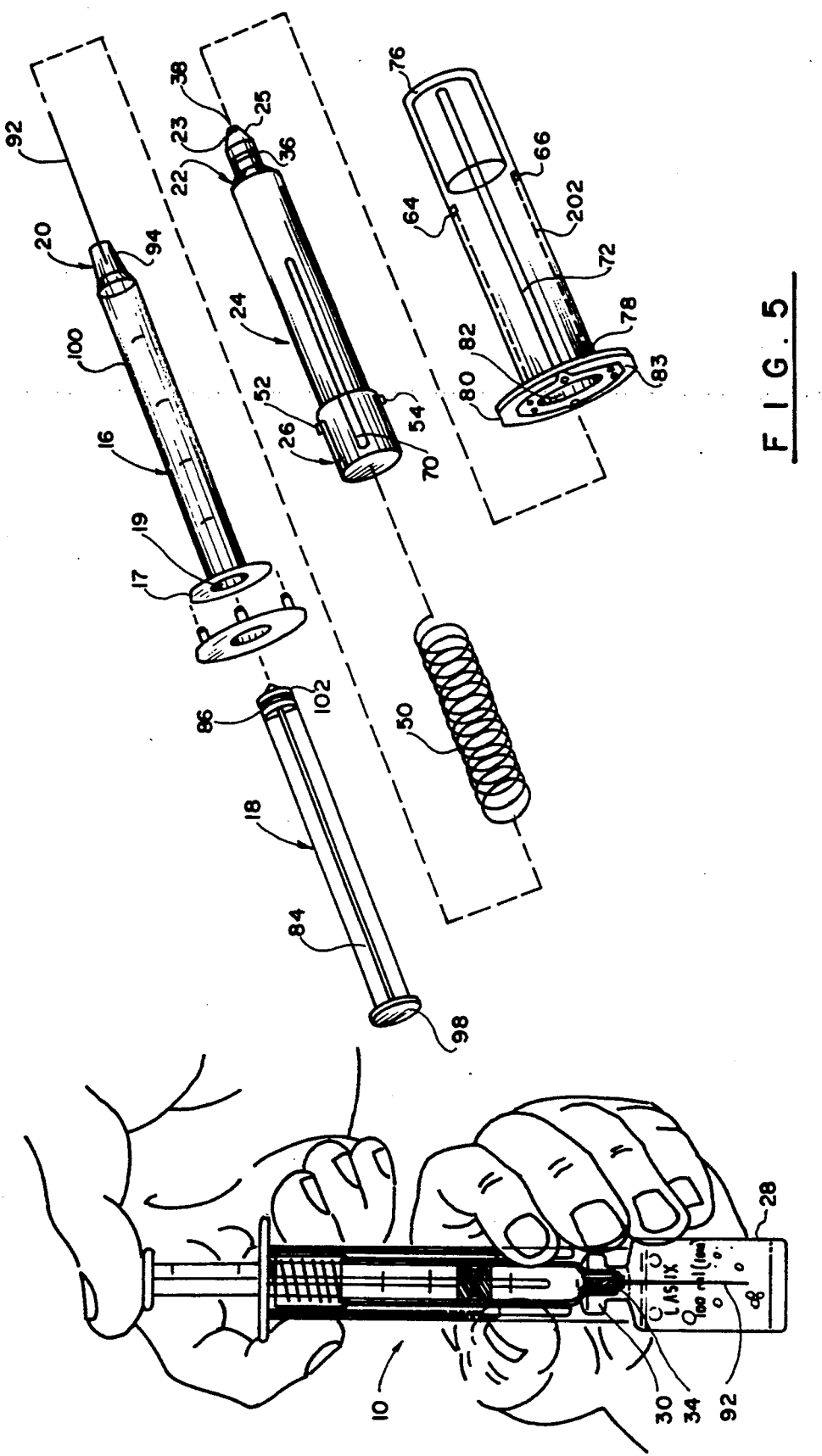

SELF-LOCKING SAFETY SYRINGE

BACKGROUND OF THE INVENTION

This invention relates to medical equipment, and more particularly to a safety syringe designed to prevent accidental needle stick injuries by medical personnel, particularly with respect to contaminated needles.

The ever increasing spread of diseases transmitted by blood and other bodily fluids, such as Acquired Immune Deficiency Syndrome and Hepatitis B, creates a real threat to medical personnel of accidental, inadvertent, puncturing of the skin by a syringe needle, which has been in contact with an infected patient and transmittal of the often fatal disease to the unfortunate medical attendant. Despite educational programs carried by many hospitals, every day somewhere in the United States at least one nurse or a medical attendant, who comes into contact with an infected syringe needle, will become punctured by such needle, while trying to dispose of the used syringe or during any other manipulation of dirty syringes.

Various attempts have been made to resolve this problem by proposing to use a protective syringe needle guard, which would cover the needle when the syringe is not in use and prevent the needle from being exposed during those times. However, such devices are expensive to manufacture, difficult to use, requiring several steps in preparing the syringe for utilization and, so far, have not found wide acceptance in the medical profession.

The present invention has a general objective of overcoming drawbacks and shortcomings associated with the prior art and provision of an inexpensive, easy to use self-locking safety syringe.

SUMMARY OF THE INVENTION

It is, therefore, an object of the present invention to provide a self-locking safety syringe which is designed to prevent exposure of the needle.

It is another object of the present invention to provide a locking device for covering the needle, which is easy to use and inexpensive to manufacture.

It is a further object of the present invention to provide a needle guard which is equipped with means to prevent free rotation of the needle guard within a protective casing.

These and other objects of the present invention are achieved through a provision of a safety guard device for a syringe needle, which comprises an elongated tubular casing having a pair of aligned diametrically opposite needle openings, the casing housing an elongated needle guard which is telescopically connected to the casing in co-axial alignment therewith and is adapted for movement between a first position, substantially covering a needle assembly of a syringe and a progressively retracted position. A pair of depressible locking tabs are attached to the needle guard and extend through the openings formed in the casing to lock the needle guard in its first position, when the syringe is not in use. A coil spring continuously urges the needle guard to the first position, the tension of the spring being overcome only by a double safety mechanism: by depressing the locking tabs and exerting a pressure on a forward end of the needle guard, so as to move the needle guard inwardly into the casing and inject the needle.

The syringe barrel is co-aligned positioned with the needle guard and is fixedly attached at its outer end, to a transverse flange of the casing.

One end of the casing is partially closed by a transverse flange having a central opening therein. A plunger which carries a syringe piston on the innermost end is received through that opening in the transverse flange and moves within the syringe barrel to create vacuum and allow drawing of medicine into the syringe.

A pair of angularly inclined abutting shoulders on the casing and the needle guard prevent complete disengagement of the needle guard from the casing.

BRIEF DESCRIPTION OF THE DRAWINGS

Reference will now be made to the drawings, wherein like parts are designated by like numerals, and wherein FIG. 1 is a schematic plan view of the device in accordance with the present invention.

FIG. 2 is a detail plan view of the locking portion of the device of the present invention.

FIG. 3 is a detail plan view taken at 90 degrees from the view shown in FIG. 2.

FIG. 4 is a schematic view illustrating the device of the present invention in use during drawing of medicine from a bottle, and immediately prior to removing the syringe from the bottle.

FIG. 5 is an exploded view of the device in accordance with the present invention.

DETAILED DESCRIPTION OF THE PREFERRED EMBODIMENT

Figure 6:
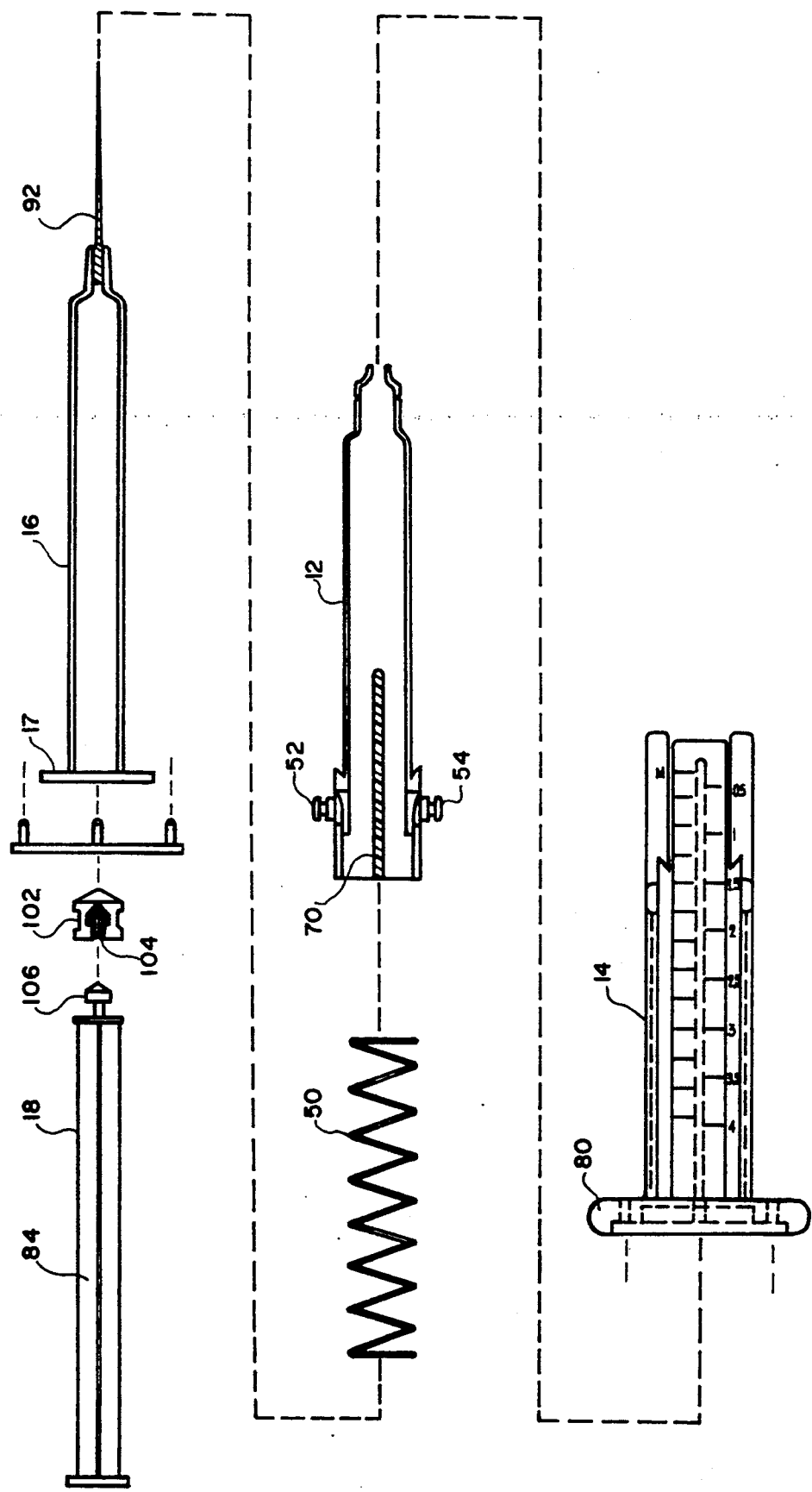
FIG. 6 is an exploded plan view of the device.
Figure 7:
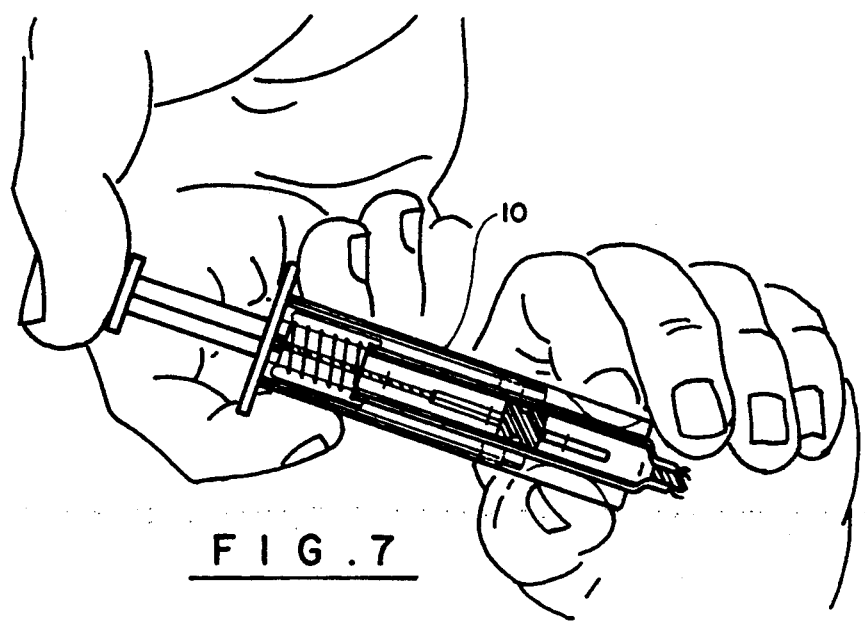
FIG. 7 is a perspective view illustrating the device of the present invention in use during an injection.
Figure 8:
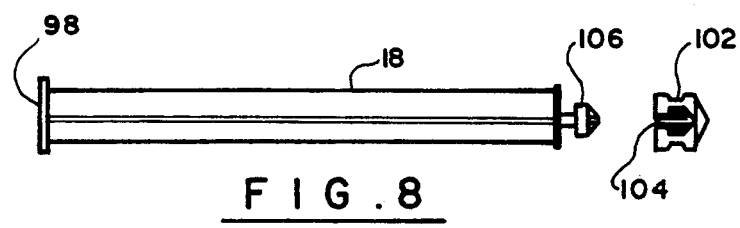
FIG. 8 is a detail view of a plunger of the syringe.
Figure 9:
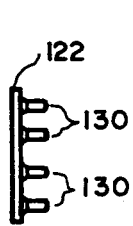
FIG. 9 is a detail end view of a sealing plate.
Figure 10:
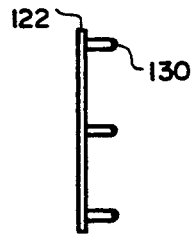
FIG. 10 is a detail side view of the sealing plate.
Figure 11:
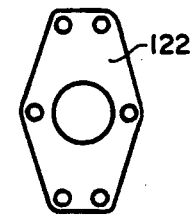
FIG. 11 is a top view of the sealing plate.

Referring now to the drawings in more detail, numeral 10 of FIG. 1 designates the device of the present invention. The device 10 comprises a needle guard 12, a barrel casing 14, a syringe barrel 16, a plunger 18, and a needle assembly 20.

The needle guard 12 comprises a first, nose portion 22, a second, middle portion 24, and a third, inner portion 26. As can be seen in the drawings, the first portion 22 is a reduced diameter portion adapted for contact with a medication bottle 28 (See FIG. 4). In some cases, the first, nose portion 22 of the needle guard 12 will contact the outer rim of the bottle top 30, while in other cases, the first portion 22 will "snap" into the bottle neck of the bottle 28, as illustrated in FIG. 4, and lock with the bottle by engaging an annular inner ridge 34 formed in the bottle 28 neck by an annular groove 36. The nose portion 22 has a forward most end 23 which has a progressively small diameter and conically flaring wall 25.

A central opening 38 is made in the outermost end of the first portion 22 to allow the needle 92 to pass therethrough during an injection, or drawing of medicine from the bottle 28.

The middle portion 24 of the needle guard 12 has an enlarged diameter in comparison with the first portion 22 and has a greater length, so as to completely cover the needle assembly 20 and extend, to some degree, in a telescopical relation within the casing 14.

The innermost end of the middle portion 24 terminates with an outwardly, annularly extending shoulder 44 which is formed at a sharp angle to the annular wall of the middle portion 24 and extends outwardly therefrom.

The third, still greater diameter portion 26 extends co-axially with the portion 22, 24 and is provided with a central opening 42 having a diameter substantially greater than a diameter of the syringe barrel 16, which is positioned inside the needle guard 12 and the casing 14. It should be noted that the needle guard middle portion 24 is also hollow and has a central opening which is slightly greater than the outer diameter of the syringe barrel 16.

An annular groove 48 is formed in the shoulder 44, the groove receiving one end of a tension spring 50 (FIG. 2), which surrounds the barrel 16 and urges at its distant end against the shoulder 44 and the groove 48 formed therein.

Integrally formed with an inner wall (FIG. 3) of the inner portion 26 are a pair of locking tabs 52 and 54, which are designed to be compressed by fingers of the user, so as to force them inwardly towards the center of the needle guard 12. A pair of openings 56 and 58 are formed forwardly from the locking tabs 52 and 54 to allow for full compression of the tabs.

It is preferred that the tabs 52 and 54 be mounted on tab supports 60, 62 in such a manner, as to allow spring-like movement of the tabs outwardly through openings 64 and 66, which are made in the wall of the casing 14 in alignment with the tabs 52, 54.

When the syringe needle 92 is covered by the needle guard 12, the locking tabs 52 and 54 extend outwardly through the openings 64 and 66 and prevent movement of the needle guard 12 in relation to the casing 14. However, when the tabs 52 and 54 are depressed to a degree sufficient to move them from their position illustrated in FIG. 3 inwardly, such that the outward surface of the tabs 52 and 54 can recess inwardly into locking tab grooves 200 and 202 of the casing 14, the telescopical movement between the needle guard 12 and the casing 14 becomes possible.

The inner portion 26 of the needle guard 12 is further provided with at least one outwardly extending ridge, or runner, 70 which extends in a parallel relationship to the central axis of the needle guard 12. A matching elongated groove 72 is formed in the interior wall of the casing 14 to receive the runner 70 therein and to prevent the needle guard 12 from rotating about its axis and twisting, while moving longitudinally in telescopical relationship within the casing 14. The runner/groove assembly helps prevent misalignment of the locking tabs 52 and 54 during operation, such that it is assured that locking tabs 52 and 54 will spring outwardly, locking through the openings 64 and 66.

The casing 14 is formed as an elongated tubular body having a pair of diametrically opposite openings 64 and 66, as was described above, adapted to receive the locking tabs 52 and 54 therethrough. One end 76 of the casing 14 is open to receive the needle guard 12 therethrough. The opposite end 78 of the casing 14 is partially closed by an enlarged diameter flange plate 80 which has a central opening 82 therein in co-alignment with a central axis of the casing 14.

The opening 82 has an outer perimeter symmetrical in shape to that of the syringe barrel 16. An end plate 17 of the barrel 16 is sized and shaped to "snap" into a specially recessed groove 81 formed in the outer surface 83 of the flange plate 80, such that opening 19 of the syringe barrel is in co—alignment with the central axis of the casing 14.

Figure 12:
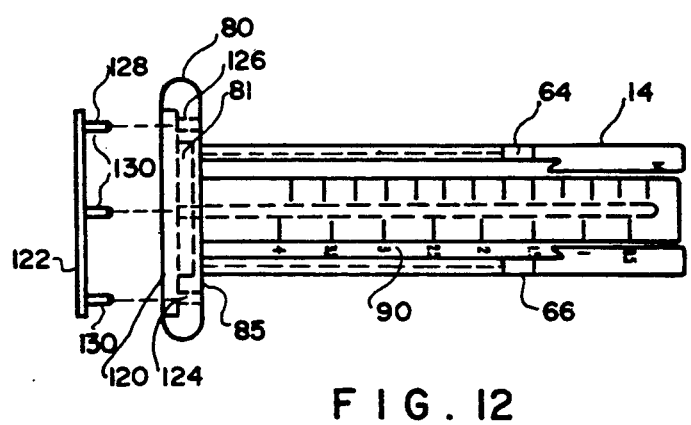
FIG. 12 is a detail exploded plan view of a barrel casing and sealing plate.

A second recessed groove 120 is formed in the outer surface 83 of the flange plate 80 to receive a sealing plate 122 therein. The groove 120 is greater in overall surface area than the groove 81, since the size of the sealing plate 122 is greater than that of the end plate 17. The groove 120 is not as deep as the groove 81, as can be better seen in FIG. 12.

Extending inwardly towards the inner surface 85 of the flange plate 80 are a plurality of openings 124 which extend from the bottom surface of the groove 120 towards the surface 85 of the flange plate 80. The openings 124 are formed closer to the outer perimeter of the flange plate 80 and do not communicate with the groove 81.

The walls defining the openings 124 are provided with angularly oriented extensions 126 which are adapted to engage matching projections 128 formed on pins 130. The pins 130 serve as attachment members for a sealing plate 122, which is sized and shaped to snugly fit within the groove 120, so as to prevent disengagement of the syringe barrel 16 from the casing 14. When "snapped" in place, the sealing plate 122 forces the pins 130 into the corresponding openings 124.

It should be noted, that the projections 128 are oriented in an opposite direction in relation to the extensions 126. In this manner, the sealing plate 122 and the syringe barrel 16 cannot be separated from the casing 14 without using extreme force.

Although the preferred embodiment illustrates the use of six transversely oriented pins 130 with the sealing plate 122, it will be apparent to those skilled in the art, that any other number of pins can be used for the purpose stated above. The pins 130 can be equidistantly located on the sealing plate 122, or grouped in pairs, as shown in the preferred embodiment, wherein a non-circular shape of the plate 122 is used.

The tension spring 50 urges with its second end against the inner surface of the flange plate 80 and, in its normally expended position, forces the needle guard 12 outwardly from the casing 14 to a position illustrated in FIG. 1, fully covering the needle assembly 20.

When the tabs 52 and 54 are compressed, and a pushing force is applied to the nose portion 22, the needle guard 12 moves against the force of the spring 50 inwardly in relation to the casing 14 to a position illustrated in FIG. 4, introducing the needle 92 and allowing to perform an injection or to withdraw medication from the bottle 28.

The spring 50, however, is strong enough to continuously urge the needle guard 12 outwardly to a position shown in FIG. 1, when the tabs 54 and 56 are not compressed, that is when they extend outwardly from their openings in the casing 14. The spring 50 is made soft enough to permit performing of injections to a patient without undue pressure on the tissue around the injection site.

The casing 14 is provided with an inwardly extending shoulder 88 (see FIG. 2) which is inclined at an angle to match the angle of the outwardly extending shoulder 40 of the needle guard 12. The shoulder 88 acts as a stop, limiting movement of the needle guard 12 in relation to the casing 14 outwardly therefrom. Thereby, full disengagement of the needle guard 12 from the casing 14 is prevented.

Mounted inside the needle guard 12 and extending substantially through the entire length is a syringe barrel 16, which is similar in size and construction to a conventional syringe barrel and can be of a size to accept three cc of liquid, or more. A measuring indicia 90 (see FIG. 12) can be imprinted on the outside of the casing 14, or the syringe barrel 16 to permit precise measuring of the liquid introduced into the syringe barrel 16. Mounted on the forward end of the barrel 16, in a fixed relationship thereto, is the needle assembly 20 which has a needle 92 extending outwardly from a securing portion 94 thereof. The needle assembly 20 is similarly engaged with the barrel 16 to prevent introduction of air into the hermetically sealable interior of the barrel 16.

A syringe plunger 84 is received in slidable engagement within the barrel 16, and has a length greater than the length of the syringe barrel 16, extending at 96 outwardly from the casing 14 and terminating with an enlarged diameter end plate 98. The plunger 84 carries a piston assembly 86 on its inward portion, which frictionally engages the interior wall of the syringe barrel 16 and allows to create a vacuum in the most forward end 100 of the barrel 16, when moving outwardly from the barrel 16.

The piston assembly 86 is formed with a sealing member 102 for sealing with the syringe barrel wall, and to insure that no air is allowed to escape past the sealing member 102. If desired, a measuring indicia can also be printed on the plunger 84. It is preferred, therefore, that the casing 14 be formed from a transparent material to allow reading of the measuring indicia by the user. The sealing member 102 has an opening 104 therein which is sized and shaped to receive an outwardly protruding rod 106, which is affixed to the elongated portion 84 of the plunger 18.

In operation, a nurse removes the device 10 from its sterile packaging, wherein the device 10 is kept in a locked position illustrated in FIG. 1 until ready to use. The nurse then compresses the tabs 52 and 54 and moves the nose 22 in contact with the neck of a medication bottle 28. By slightly pushing against the force of the spring 50, the user allows the needle guard 12 to move inwardly, telescopically in relationship to the casing 14 and introduces the sharp needle 92 into the medication bottle 28.

A continuous pressure on the flange plate 80 will cause the needle 92 to further penetrate into the interior of the medication bottle 28. During that time, the tabs 52 and 54 are fully compressed and travel with the needle guard 12 along the locking tab grooves 200 and 202 within the casing 14. The spring 50 is compressed to a position shown in FIG. 4, and the fingers of the user are positioned at the base of the syringe, so as not to cover openings 64 and 66. The nurse operates the plunger 84, moving it outwardly from the syringe barrel 16 and allows introduction of the medication into the syringe barrel 16.

Once the necessary amount is withdrawn, the nurse removes safety syringe 10 from the medication vial, taking care not to cover openings 64 and 66, and the spring 50 forces the needle guard 12 outwardly, again covering the needle 92, and automatically locking it in its most extended position.

When the nurse contacts the skin of the patient in preparation to give the injection, she again compresses the tabs 52 and 54 and, by holding and pressing casing 14 towards skin of patient, causes the needle guard 12 to move inwardly into the casing 14. The nurse injects the needle 92 into the patient. Continuous pressure inward, while holding casing 14, forces the needle into the body tissue of the patient. The plunger 84 is then again operated by pushing it inwardly to force the medication out of the syringe barrel 16 into the patient's tissue through the needle 92. The injection proceeds in a conventional manner.

Once this operation is completed, the nurse again pulls on the casing 14 withdrawing it from the patient, while simultaneously the spring 50 extends again and forces the needle guard into a position completely covering the needle 92.

As will be appreciated, the device 10 of the present invention has a double security locking system: in the form of the locking tabs 52 and 54 and of the engagement between the casing 14 and the needle guard 12, whereby the needle 92 cannot be injected until pressure is applied to the nose portion 22, while the locking tabs 52 and 54 are compressed.

Changes and modifications can be made within the design of the present invention. For example, the sealing plate 132 can be made without the locking pins 130. In such a case, the sealing plate will simply "snap" into the groove 120, similar to the end plate 17 of the syringe barrel 16.

The device 10 can be made from clear, transparent plastic, with the exception, of course, of the needle 92. The piston assembly 86 can be made from a resilient compressible material, such as rubber, or other suitable material. The spring 50 can be made from steel, or a material having similar physical properties.

Many other changes and modifications can be made within the general design of the present invention without departing from the spirit thereof. I, therefore, pray that my rights to the present invention be limited only by the scope of the appended claims.

I claim:

1. A self-locking safety syringe device, comprising:
   an elongated tubular casing;
   a syringe barrel having a needle assembly affixed thereto, said syringe barrel being securely attached to one end of the casing;
   an elongated hollow needle guard telescopically coaxially engaged with the casing, said needle guard being movable between a first position, substantially covering the needle assembly and a second, retracted position, exposing the needle assembly;
   a resilient depressible means for locking the needle guard in the first position, said locking means being carried by the needle guard;
   a tension spring means continuously urging the needle guard to the first position, thereby preventing accidental movement of the needle guard into the second position even after the locking means have been depressed; and
   means for preventing misalignment of the needle guard in relationship to the casing, said means comprising at least one outwardly extending runner mounted on an outer surface of the needle guard and at least one elongated groove formed in an interior wall of the casing, the groove being sized and shaped to receive the runner in slidable engagement therein.

2. A self-locking safety syringe device, comprising:
   an elongated tubular casing;

a syringe barrel having a needle assembly affixed thereto, said syringe barrel being securely attached to one end of the casing;

an elongated hollow needle guard telescopically co-axially engaged with the casing, said needle guard being movable between a first position, substantially covering the needle assembly and a second, retracted position, exposing the needle assembly;

a resilient depressible means for locking the needle guard in the first position, said locking means being carried by the needle guard;

a tension spring means continuously urging the needle guard to the first position, thereby preventing accidental movement of the needle guard into the second position even after the locking means have been depressed;

means for limiting outward movement of the needle guard in relationship to the casing; and wherein said limiting means comprises an outwardly extending annular shoulder formed on the needle guard and an inwardly extending shoulder formed in the casing, said shoulders abutting each other, when the needle guard is moved to its most outwardly extending position in relation to the casing.

3. The device of claim 2, wherein said shoulder of the needle guard and the shoulder of the casing extend at a matching inclined angle in relation to a longitudinal axis of the device.

4. The device of claim 3, wherein said needle guard has a first, nose portion, a second, middle portion, and a third, inner portion, and wherein said shoulder is formed at a line of attachment of the middle portion to the inner portion.

5. A self-locking safety syringe device, comprising:
an elongated tubular casing;
a syringe barrel having a needle assembly affixed thereto, said syringe barrel being securely attached to one end of the casing;
an elongated hollow needle guard telescopically co-axially engaged with the casing, said needle guard being movable between a first position, substantially covering the needle assembly and a second, retracted position, exposing the needle assembly;
a resilient depressible means for locking the needle guard in the first position, said locking means being carried by the needle guard;
a tension spring means continuously urging the needle guard to the first position, thereby preventing accidental movement of the needle guard into the second position even after the locking means have been depressed;
wherein said casing has a first open end, through which the needle guard extends, and a second, partially closed end, and wherein an enlarged diameter flange is mounted on the second end, said flange being provided with a central opening which is sized and shaped to receive the syringe barrel therethrough, the syringe barrel having a syringe piston on its innermost end, and an end plate on its outermost end, said end plate engaging the flange in a fixed engagement; and
wherein said flange is provided with a first recessed groove, which is sized and shaped to receive the end plate in a locking engagement therein.

6. The device of claim 5, further comprising a sealing plate adapted to cover the end plate locked within the flange.

7. The device of claim 6, wherein said flange is provided with a second groove which is sized and shaped to receive the sealing plate in a locking engagement therein.

8. The device of claim 7, wherein said sealing plate is provided with a plurality of transversely extending pins, and said flange is provided with a plurality of matching openings to receive the pins in a fixed engagement therewith, thereby securely attaching the sealing plate to the flange.

9. A self-locking safety syringe device, comprising:
an elongated tubular casing;
a syringe barrel having a needle assembly affixed thereto, said syringe barrel being securely attached to one end of the casing;
an elongated hollow needle guard telescopically co-axially engaged with the casing, said needle guard being movable between a first position, substantially covering the needle assembly and a second, retracted position, exposing the needle assembly;
a resilient depressible means for locking the needle guard in the first position, said locking means being carried by the needle guard;
a tension spring means continuously urging the needle guard to the first position, thereby preventing accidental movement of the needle guard into the second position even after the locking means have been depressed, said tension spring means comprising a coil spring mounted in circumferential relationship about the syringe barrel; and
wherein an outwardly extending shoulder is formed on the needle guard, said shoulder being provided with an inner groove, and wherein one end of the coil spring is received in said annular groove.

10. The device of claim 9, wherein one end of the casing is partially closed with a transverse flange, said flange having an inner surface and an outer surface.

11. The device of claim 10, wherein a second end of the coil spring urges against the inner surface of the transverse flange.

12. A safety guard device for a syringe needle, comprising:
an elongated tubular casing having a first open end and a second, partially closed end, and wherein a transverse flange is fixedly attached to the second end of the casing, said transverse flange having a central opening extending therethrough, said opening being adapted for receiving a syringe barrel in co-axial engagement, said syringe barrel having a needle assembly attached to one of its ends and an end plate secured to its other end, said end plate fixedly engaging the transverse flange;
an elongated hollow needle guard telescopically co-axially engaged with the casing, said needle guard being movable between a first position, substantially covering the needle assembly and a second, retracted position, away from the needle assembly, said needle guard having a first, nose portion, a second, middle portion, and a third, inner portion, and wherein an outwardly extending shoulder is formed at a line of attachment of the middle portion to the inner portion, said shoulder being provided with an annular groove;
a resilient depressible locking means for locking the needle guard in the first position, said locking means being carried by the needle guard, said locking means comprising a pair of depressible locking tabs fixedly attached to the needle guard and extending outwardly through corresponding aligned openings formed in the casing;

a tension spring means continuously urging the needle guard into the first position, thereby preventing accidental movement of the needle guard into the second position, even after the locking means have been depressed;

means for preventing misalignment of the needle guard in relationship to the casing, said means comprising at least one outwardly extending runner mounted on an outer surface of the needle guard and at least one elongated groove formed in an interior wall of the casing, the groove being sized and shaped to receive the runner in slidable engagement therein.

13. The device of claim 12, wherein an inwardly extending shoulder is formed in the casing, said shoulder abutting the outwardly extending shoulder of the needle guard to limit outward movement of the needle guard in relationship to the casing.

14. The device of claim 13, wherein said shoulder of the needle guard and the shoulder of the casing extend at an inclined angle in relation to a longitudinal axis of the device.

15. The device of claim 12, wherein said tension spring means comprises a coil spring mounted in circumferential relationship about the syringe barrel.

16. The device of claim 8, wherein one end of the coil spring is received in an annular groove formed in the outwardly extending shoulder of the needle guard, while the second end of the coil spring urges against an inner surface of the transverse flange attached to the casing.

17. The device of claim 12, wherein said flange is provided with a first recessed groove adapted to receive the end plate in a fixed engagement thereto.

18. The device of claim 17, further comprising a sealing plate for covering the end plate locked within the first groove.

19. The device of claim 18, wherein said flange is provided with a second recessed groove sized and shaped to receive the sealing plate in a locking engagement therein.

20. The device of claim 18, wherein said end plate is provided with a plurality of transverse pins, and said flange is provided with a plurality of matching openings, said pins being adapted for a fixed engagement within said openings.

* * * * *